United States Patent [19]

Oscarsson

[11] Patent Number: 5,352,214

[45] Date of Patent: Oct. 4, 1994

[54] TUBING CLAMB TO CONTROL FLOW THROUGH COMPRESSIBLE TUBING

[76] Inventor: Rolf A. Oscarsson, 1550 Winchell Dr., Hudson, Ohio 44236

[21] Appl. No.: 35,084

[22] Filed: Mar. 22, 1993

Related U.S. Application Data

[63] Continuation-in-part of Ser. No. 618,236, Nov. 26, 1990, abandoned.

[51] Int. Cl.⁵ .............................................. A61M 5/00
[52] U.S. Cl. ........................................ 604/250; 251/9; 251/230; 251/231; 251/251; 251/286; 604/248; 604/32; 604/34
[58] Field of Search ............... 604/30, 32, 33, 34, 604/65, 207, 246, 248, 249, 250, 251, 256, 407; 128/DIG. 13; 251/9, 4, 95, 101, 230, 231, 251, 286, 304, 312

[56] References Cited

U.S. PATENT DOCUMENTS

| | | |
|---|---|---|
| 2,285,821 | 6/1942 | Maloney . |
| 2,595,511 | 5/1952 | Butler . |
| 3,299,904 | 1/1967 | Burke ................................. 604/250 |
| 3,550,900 | 12/1970 | Rolin ...................................... 251/9 |
| 3,915,167 | 10/1975 | Waterman . |
| 3,960,149 | 6/1976 | Bujan . |
| 4,247,076 | 1/1981 | Larkin .................................... 251/9 |
| 4,660,802 | 4/1987 | Oscarsson .............................. 251/9 |

Primary Examiner—C. Fred Rosenbaum
Assistant Examiner—Ronald K. Stright, Jr.
Attorney, Agent, or Firm—Oldham, Oldham & Wilson Co.

[57] ABSTRACT

A tubing clamp controlling flow within compressible tubing passing through the clamp which is adapted for inserting the tubing sidewise into the clamp upon opening of a hinged side wall. An adjustable flow controller overlies the tubing and is adapted to rotate, bear upon and squeeze the tubing for precise flow control. A lever arm to actuate the flow controller is in ratcheting engagement with an arcuate bar to hold the lever arm and cylindrical surface of the flow controller in the desired rotative position. The selected position of the lever arm can then be recorded. The tubing clamp can be constructed as a one-piece structure by use of a single mold and prepared as a kit to facilitate use for medical purposes. The assembly of the clamp is thus simplified and the method for controlling flow is accomplished by a series of simple steps.

15 Claims, 2 Drawing Sheets

TUBING CLAMB TO CONTROL FLOW THROUGH COMPRESSIBLE TUBING

CROSS-REFERENCE TO EARLIER FILED APPLICATION

This application is a continuation-in-part of application Ser. No. 07/618,236, filed Nov. 26, 1990 now abandoned.

TECHNICAL FIELD

This invention pertains to a medical clamp of the type commonly used to control flow through tubing when transfusing blood or other medical fluids, during dialysis or clinical monitoring procedures.

BACKGROUND OF THE INVENTION

Medical clamps for constricting and thereby regulating flow through tubing are generally small and lightweight, so that the clamps can be supported by the tubing itself. In the medical field, such clamps are commonly used as part of a flow control tubing system of regulating medical fluids passing through the system. Systems of this type, as well as other medical laboratory systems, frequently use compressible plastic tubing with flow control clamps to control flow through the tubing.

Such tubing clamps are set to constrict the tubing for a prescribed flow through the tubing, for example, drops per minute or ml/hr. A common medical application would be the infusion of medical fluid into a patient's venous system.

When in use, the clamps are frequently removed, relocated and reinstalled on the tubing system when the patient is moved or the system is taken down and set up again for purposes of changing medications, dosages or cleaning.

One of the major problems associated with previous clamps employed for similar purposes is the requirement of threading the plastic tubing through the clamp or assembly, like threading a needle, which in most cases is typically done by the manufacturer and not the end user.

The prior art clamps which can be opened for sidewise installation of tubing usually have more than one component. This sometimes resulted in the loss or misplacing of one of the separable components prior to assembly with delay in the installation until the missing component is found.

Also, former tubing clamps may lack sufficient variability or precision in regulating flow. For instance, former versions occasionally lack the required degree of precision in flow control between certain settings; and, medical personnel using the former clamps may have encountered difficulty in setting the clamp to the prescribed flow rate.

In addition to the foregoing disadvantages, some prior flow control devices were not provided with any visual means to indicate the adjusted setting of the device at the prescribed flow rate. Thus when such flow control devices of the prior art were disconnected from the tubing system, for example, when taken down for adjusting or putting a new bag or bottle in the system, it would then be necessary to manually reset the device to provide a similar drip rate. Such resetting is time consuming, leads to inaccuracy and represents a negative factor in the prior flow control devices.

Finally, the former flow control devices, which had more than one component and were manufactured from plastic molds, required a separate mold for each component of the device; and the components of the clamp were separate pieces when manufactured. This increases manufacturing costs and ultimately the purchase price for the item. An important advantage of manufacturing the clamp in a single mold as a one-piece structure is that all the required pieces of the clamp are together at the time of use. In a medical setting, this factor is important for it decreases the possibility that one component of the clamp might be lost or unavailable, thereby rendering the device useless.

SUMMARY OF THE INVENTION

Accordingly, a principal object of the invention is to provide a tubing clamp having a body adapted for sidewise insertion of small gage elastic tubing with a rotatable flow controller for constricting the tubing in the body to a prescribed flow rate.

Another object of the invention is to provide a tubing clamp with a hingeably affixed second side wall capable of being opened to allow quick and easy sidewise insertion of the tubing into the clamp and then closed and locked in position around the tubing.

Still another object of the invention is to provide a tubing clamp with a rotatable flow controller having cylinder portion with a cylindrical surface at the first end and a lever arm radiating a distance away from the cylinder portion at the second end. In addition to the foregoing, the invention has as an objective greater precision in flow control by means of gradual adjustment of a lever arm, so that a relatively large movement of the lever arm results in only a minor rotation of the cylinder portion. And rotation of the flow controller, with its cylindrical surface contacting the tubing, directly affects the flow rate.

A further objective of the invention is to provide longitudinal slots grooved in each of the side walls of the body member to receive journal ends projecting axially from the sides of the cylinder portion of the flow controller to facilitate insertion of the tubing and flow controller in the body.

A still further objective of the invention is to provide a tubing clamp having, in its most general embodiment, a plane passing through the longitudinal slots and the plane of the slots, if extended, intersecting the plane of the bottom wall, if extended.

Another object, in a first modification of the invention, is to provide a tubing clamp wherein the bottom wall is elevated from the posterior end toward the anterior end of the body to allow gradual tightening of the flow controller as it bears upon the compressible tubing lying on the bottom wall.

The invention has the further object of maintaining the prescribed flow controlling position after it has been attained by providing anterior and posterior braces projecting from either end of the first side wall, the braces connected at their outer ends by an arcuate bar coaxial with a line passing transversely through the center of each of the longitudinal axes of each of the slots, whereby the lever arm extending to, but not contacting the arcuate bar, is maintained in selected position by frictional contact with the tubing.

Another objective, in a second modification of the invention, is to provide a lever arm having sufficient length to extend over the arcuate bar and to include on the arcuate bar a series of ratchet teeth along its entire length and a detent on the lever arm. The detent projects from the outer end of the lever arm to contact and engage the ratchet teeth of the arcuate bar and lock the lever arm in place against return rotative movement, whereby the flow controller is maintained in a selected rotative position.

A still further object of the invention is to provide a tubing clamp with visual means to record and reinstitute the same flow rate, upon removal and reinstallation of the clamp by means of the arcuate bar having indicia markings along its entire length, which indicia or indicators serve as a memory device relating to the position or placement of the lever arm when the tubing clamp is dismantled.

A still further object of the invention is manufacture of the tubing clamp with simple, inexpensive manufacture of the clamp in a single one-piece structure with a single mold. A related object is to facilitate and simplify assembly, since the tubing clamp constructed as a single unit provides some assurance that all required parts are available at time of assembly. Furthermore, such a tubing clamp with one-piece construction can be packaged, marketed and sold as a kit.

The subject invention therefore comprises an improved flow control device which overcomes the foregoing problems and others and allows for manufacture of a one-piece clamp in a mold for reduced manufacturing costs and for assurance that all components of the clamp are together at time of assembly.

The tubing clamp when manufactured as a one-piece structure is forms a molded array of the clamp, which includes a flow controller detachably coupled to the body of the clamp by a tear tab for easy separation, insertion and use as a movable component of the clamp. The tubing clamp is capable of being opened for sidewise insertion of tubing and flow controller and then closed to retain the controller in position overlying and bearing upon the tubing.

In accordance with one aspect of the invention, the tubing clamp of the type referred to above is comprised of an elongated U-shaped body member (when the body of tubing clamp is in closed arrangement), having two side walls and a bottom wall, the first side wall durably affixed to the bottom wall and the second side wall hingably affixed to the bottom wall, so that the second side wall of the body may be opened for insertion of tubing upon the bottom wall. The flow controller can be removably placed in the channel defined by the body with the controller overlying the tubing. The second side wall is then closed in position approximately parallel to the first side wall, thereby and the flow controller can be rotated within the body. In another aspect of the invention, the tubing clamp also has retaining means for retaining the flow controller in a selected flow controlling position.

In accordance with a further aspect of the invention, a flow controller having first and second ends has a cylinder portion with a cylindrical surface at the first end. The cylindrical surface of the flow controller overlies and is in direct contact with the tubing while rotatably mounted between the two side walls of the body. A pair of journal ends project axially from each of the sides of the flow controller and extend into opposed longitudinal slots grooved on the inner surfaces of the side walls of the body. The slots are approximately parallel to the tubing lying in the channel.

The longitudinal slots have a plane, and that plane passing through the longitudinal slots, if extended, would intersect the plane of the bottom wall, if extended. Each slot has a notched opening to facilitate insertion of the journal ends into the slots, so that the slots are disposed for slidably and rotatably mounting the flow controller between the side walls, and upon closing the second side wall, to hold the controller and body members together in assembled rotative relation.

In a first modification of the invention, the bottom wall is elevated at one end, so that as the flow controller rotates and travels in the channel, it tightens against the elevated end of the bottom wall to squeeze and constrict the underlying tubing.

A still further aspect of the invention comprises a row of gear teeth projecting from one side of the flow controller to engage gear teeth which project from the second side wall, so that as the flow controller slides and rotates within the channel, it engages the gear teeth, travels along the bottom wall and tightens against the bottom wall to squeeze the compressible tubing against the bottom wall.

The second side wall is hingeably affixed to the bottom wall with clamp material to allow repeated opening and closing of the second side wall. The hinge is preferably constructed of a polymeric material which increases in strength upon continued and repeated flexion. One such material is polypropylene.

The tubing clamp of the invention includes anterior and posterior braces which project from either end of the first side wall of the body. The braces are connected at their ends by an arcuate bar which is coaxial with a line passing transversely through the center of each of the longitudinal axes of each of the slots.

A pair of lock plates project from the outermost ends of the second side wall, and a pair of lock arms project from the anterior and posterior braces near the ends of the first side wall; and flexible locking caps are provided at the end of each lock arm. The locking caps are disposed to receive and grip the lock plates projecting from the second side wall to secure the second side wall in closed position essentially parallel to the first side wall.

In yet another aspect of the invention, the lock arms are disposed at a distance from the bottom ramp so that insertion of the compressible tubing over the bottom ramp and under each lock arm effectively guides and holds the compressible tubing in the channel formed by the U-shaped body member.

Further objects and advantages of the invention will be apparent from the following detailed description of preferred species thereof and from the accompanying drawings.

DESCRIPTION OF THE PREFERRED EMBODIMENTS

The tubing 30 to be clamped for controlling flow is comprised of elastically compressible plastic tubing commercially known as Tygon (TM) tubing commonly employed in catheter systems.

Figure 1:
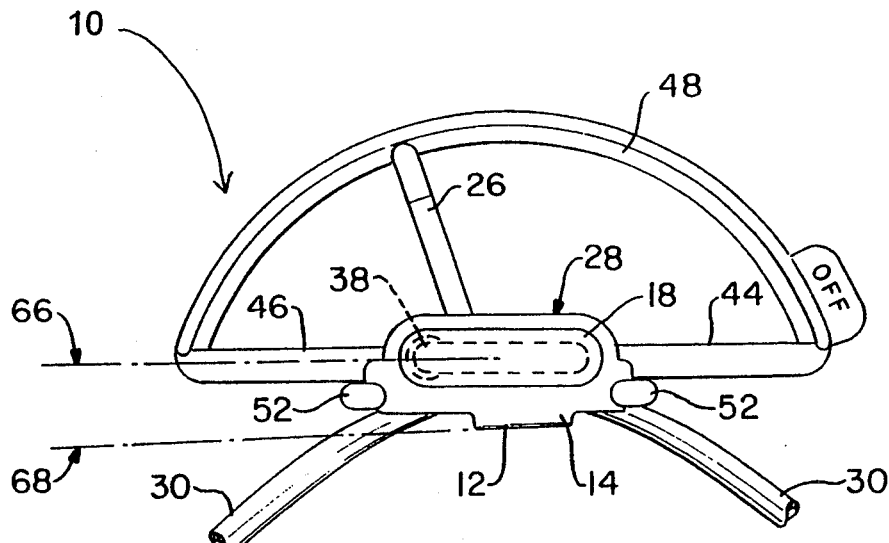
FIG. 1 is a frontal view on enlarged scale of the tubing clamp in operative array with the body in closed arrangement, the compressible tubing positioned within the clamp ready for use and flow control by means of actuating the lever arm of the flow controller.

Reference to FIG. 1 indicates the clamp 10 in operative array with the body 56 in closed arrangement. The section of tubing 30 is inserted in the tubing clamp 10 which in operation can be adjusted to compress and occlude the elastic tubing in the clamp to the extent necessary to provide the desired rate of flow, e.g., drops per unit time interval, through a respective tubing section.

Figure 3:
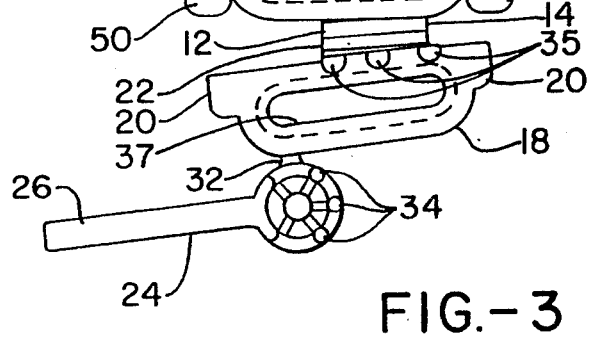
FIG. 3 is an enlarged scale frontal view of the tubing clamp as manufactured in one-piece structure with all members coupled as a single unit to form the molded array of the clamp.
Figure 4:
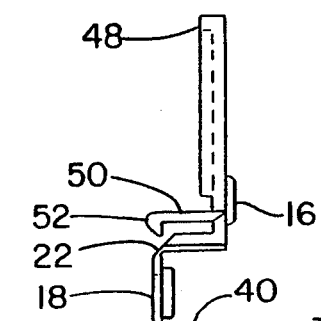
FIG. 4 is an end view of the tubing clamp in the same inoperative, molded array shown in FIG. 3.
Figure 5:
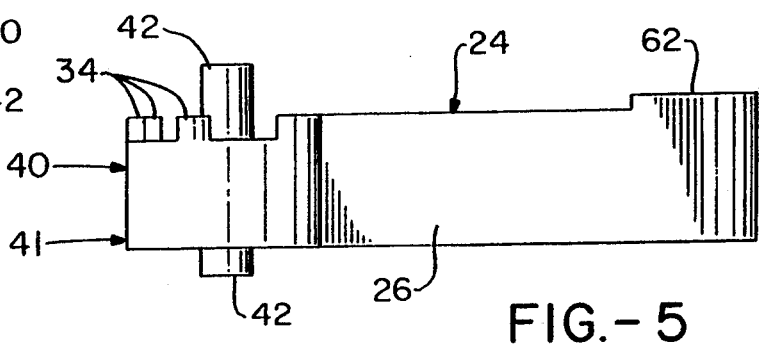
FIG. 5 is an exploded side view of the flow controller demonstrating the lever arm, cylinder portion, cylindrical surface, journal ends and gear teeth.

The entire tubing clamp 10 is constructed from one mold as a one-piece structure as shown in FIG. 3 and FIG. 4 including flow controller 24 detachably attached to body 56 by a thin tear tab 32 formed of clamp material, to facilitate location and assemblage of components. When molded as such, the clamp is in a generally flat, inoperative or molded array.

Figure 2:
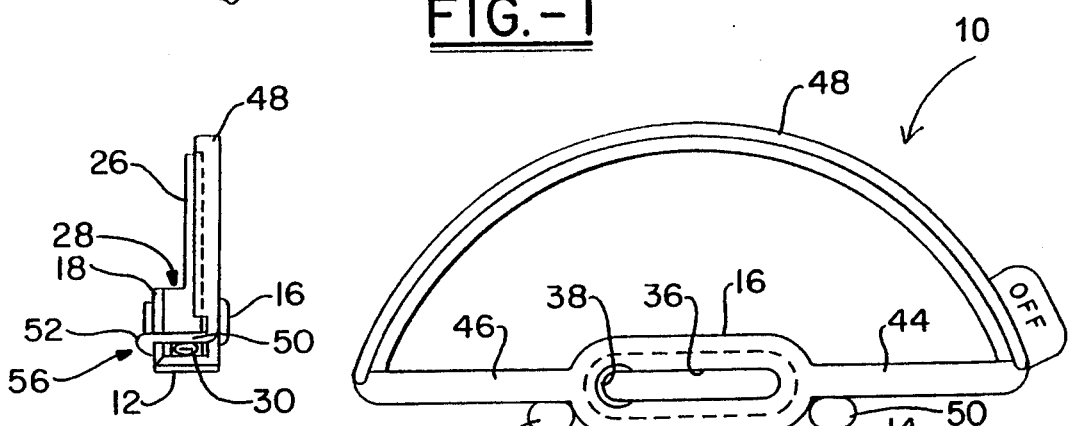
FIG. 2 represents an end elevational view of the tubing clamp of FIG. 1.

The clamp is made ready for use by assembly to form an operative array of the clamp as seen in FIG. 1 and FIG. 2. The clamp 10 is comprised of a body 56, the body having a U-shaped form as viewed from one end of the clamp, when the clamp is in the assembled or operative array of FIG. 1 and FIG. 2. A bottom wall 12 and a first side wall 16 and second repositional side wall 18, together define a channel 28 open at the top and at both ends when the body is in a closed arrangement.

Figure 6:
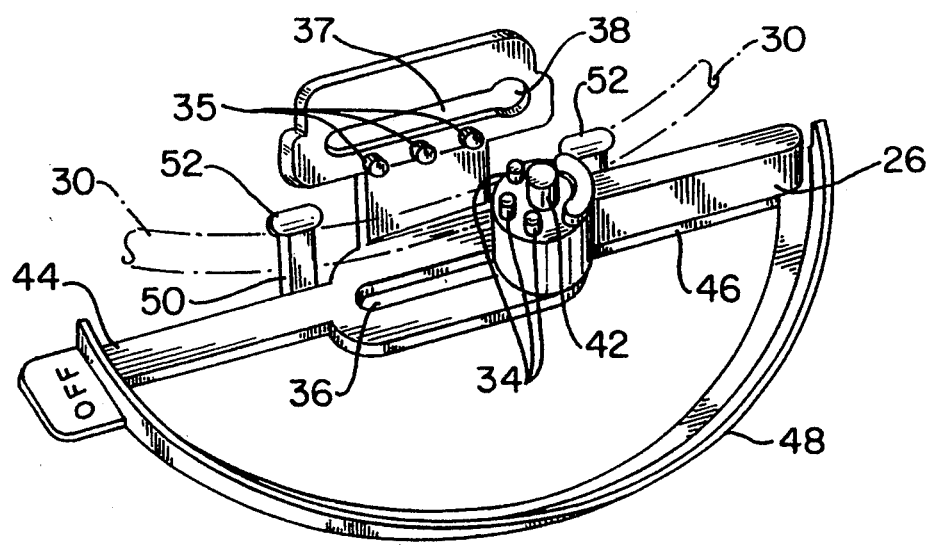
FIG. 6 represents an enlarged angle view of the clamp with the body in open arrangement, the second side wall opened to demonstrate placement of the tubing upon the bottom wall and under each lock arm.

The second side wall 18 is adapted to be opened, thereby forming an open arrangement of the body, see FIG. 6, for insertion of tubing 30 to lie upon the bottom wall 12 and a flow controller 24, to overlie the tubing, the controller slidably, rotatably and mechanically mounted to side walls 16, 18 of the body 56, such that the flow controller 24 may slide and rotate relative to the body 56.

Flow controller 24 has first and second ends with a cylinder portion 40 at its first end, the cylinder portion 40 having a cylindrical surface 41 which overlies and directly contacts the compressible tubing 30 and bears upon the tubing lying upon the bottom wall 12.

The flow controller 24 has journal ends 42 projecting axially from each side thereof, each journal end extending into a slot 36, 37 on the opposing side wall of the body 56. At one end of each of the slots 36, 37 there is a notch 38 wider than the slot itself to facilitate insertion of the journal ends 42 into the slots 36, 37.

The longitudinal slots 36, 37 form the plane 66 of the slots, when the clamp is assembled in operative array with the body in closed arrangement or U-shaped former i.e., the plane passing through both longitudinal slots, which is essentially normal to the plane of each of the side walls 16, 18. In the most general embodiment of the invention, the plane 66 of the slots, if extended, intersects with the plane of the bottom wall 68, if extended. The flow controller 24 also has a row of gear teeth 34 projecting from one side thereof to engage a row of gear teeth 35 projecting from the opposed second side wall 18.

In the first modification of the invention, there is a slight elevation of the bottom wall 12 toward the anterior end 14 of the bottom wall 12, so that as the gear teeth 34 of the flow controller 24 engage gear teeth projecting from the second side wall 18, and as the cylinder portion 40, moves in the channel 28, held in position by its journal ends 42, projecting into the slots 36, 37 the cylinder portion 40 rotates and advances along the gear teeth 34, 35, to the elevated end of the bottom wall 12; and the cylindrical surface 41 gradually tightens against the elevated end of the bottom wall 12 to squeeze and constrict the compressible tubing 30, thereby controlling flow within the tubing.

A hinge 22 for affixing the second side wall 18 to the bottom wall 12 is preferably formed of clamp material. The preferred type of hinge material should be capable of repeated flexing movements while retaining its function as a hinge. Such a living hinge may be constructed using a polymeric material. A particular material having this property is polypropelene.

A pair of lock plates 20 extend from either side of the second side wall 18. A lock arm 50 projects from both the anterior and posterior braces 44, 46. The lock arms 50 are essentially normal to the first side wall 16 and have somewhat flexible locking caps 52, at the second end of each lock arm 50.

Figure 7:
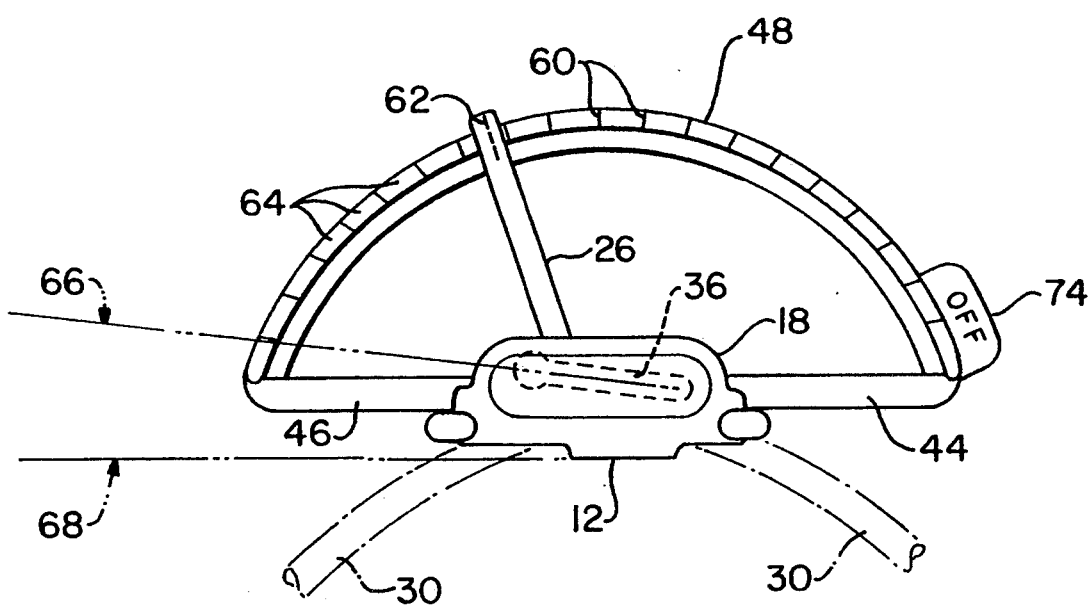
FIG. 7 is an exploded side view of the second embodiment of the clamp in operative array with the body in closed arrangement indicating the plane of the slots angled toward the plane of the bottom wall.

When the second side wall 18 is open, the body 56 may be said to be in an open arrangement; and when the second side wall 18 is closed, the body is then in a closed arrangement. The locking caps 52 are disposed to receive and grip the lock plates 20 projecting from the second side wall 18 to secure the second side wall 18 in closed snap-locked position essentially parallel to the first side wall 16. The body of the clamp is then in closed arrangement. (See FIG. 1, FIG. 2 and FIG. 7.)

The actuating arm or lever arm 26 on the flow controller 24 extends radially outward from the cylinder portion 40 of the flow controller 24. The anterior and posterior braces 44, 46 project outward on opposite sides of the first side wall 16.

Braces 44, 46 are spaced apart around the body 56 a distance corresponding approximately to the extent of angular rotatable movement of the lever arm 26 required to move the lever arm, and consequently the cylinder portion 40, from a position wherein the tubing 30 lying on the bottom wall 12 is not constricted to a position where the tubing is fully constricted. At the latter point, the tubing 30 is then fully compressed to a flattened, completely occluded condition.

The braces are connected at their outer ends by an arcuate bar 48 centered on an axis passing transversely through the center of the longitudinal axes of each of the slots 36, 37. Lever arm 26 may be constructed so that it does not project over or does not override arcuate bar 48. In that configuration, the flow controller 24 is held in a predetermined, selected position by its frictional contact with the underlying tubing. However, in the preferred embodiment, lever arm 26 of the flow controller 24 does extend sufficiently to be in contact and engage arc,ate bar 48.

And in that preferred embodiment, lever arm 26 is held in selected flow controlling position by a series of ratchet teeth 60 located on and along the length of the arcuate bar 48 engaged by a detent 62 located on the outer end of the lever arm 26, which detent engages ratchet teeth 60 to lock the lever arm in place against return rotative movement. To this end, locking faces 64 of the ratchet teeth 60 lie in respective axial planes which include the turning axis of the lever arm 26 and which face opposite the direction of return rotative movement of the lever arm to the inoperative or starting rotative position of lever arm 26.

When the lever arm 26 is rotated relative to the arcuate bar 48 by the manual operation of lever arm 26, in a direction to set the cylinder portion 40 in the prescribed flow controlling position, the detent 62 on lever arm 26 in ratcheting engagement with the ratchet teeth 60, rides over the successive ratchet teeth 60 and catches behind the locking face 64 of that ratchet tooth 60 at the desired rotative position of the lever arm 26 relative to the body member 56. The lever arm 26 is thus held in selected flow controlling position.

Disassembly of the tubing clamp 10 may be accomplished by applying force at the ends of anterior and posterior braces 44, 46 to bow the body member 56 thereby forcing lock caps 52 away from lock plates 20 to unfasten the second side wall 18 from snap-locked position whereupon the second side wall 18 can be opened an amount necessary for removal of the flow controller 24 and tubing 10 lying on the bottom wall 12 in the channel 28.

In FIG. 3 and FIG. 4, the tubing clamp is illustrated as the device would be manufactured as a one-piece structure by a single mold, with the flow controller 24 detachably attached to the second side wall 18 with a tear tab 32. The one-piece construction of the clamp 10 to form a molded array of the clamp expedites assembly and installation of tubing in the clamp, since all components are together at one location.

As shown in FIG. 6, the second side wall 18 is opened and the cylinder portion 40, with cylindrical surface 41, in contact with, but bearing only slightly on, the tubing 30 lying on the bottom wall 12. When the lever arm 26 of flow controller 24 is at that position, tubing 30 is unrestricted and open. Movement of the lever arm 26 (toward the OFF indicator 74), causes rotation of the cylindrical portion 40 of the flow controller 24 to constrict tubing 30 for precise flow control by gradual adjustment. A small movement of the lever arm 26 results in a still smaller movement of the cylindrical surface 41.

Thus, the prescribed rate of flow is attained by gradually constricting the tubing 30 and that flow rate can be recorded by indicia (not shown) inscribed along the length of the arcuate bar 48.

The occluding of the tubing 30 begins near the start of the angular movement of the lever arm 26 and associated cylinder portion 40 relative to the body member 56 in a direction to constrict the tubing 30, whereupon the flow within the tubing proceeds at a progressively slower rate during continued movement of the lever arm 26 and, concomitantly, the cylinder portion 40 relative to the body member 56.

The tubing clamp 10 described above is preferably constructed in a molding process by use of a single mold, wherein a polymeric material, such as polypropylene, is heated and formed in the mold which defines and forms the tubing clamp described above. The clamp thus constructed is in a relatively flat, inoperative or molded array, shown in FIG. 3 and FIG. 4. The clamp can then be packaged in a sealed container or envelope (not shown). The packaging should preferably be in a sterile or clean room environment, by vacuum process. The envelope or package may be a blister pack, adapted to be opened by hand and having a transparent side to see the tubing clamp within.

When in use, the clamp 10 is removed from the package and the tear tab 32 is broken to separate the flow controller 24 from the body 56 of the clamp in order to assemble the clamp and form it in an operative array.

In order to form the clamp in operative array, the tubing 30 is first positioned over the bottom wall 12 and under the lock arms 50. The flow controller 24 is then installed into the body to overlie the tubing with the cylindrical surface 41 of the cylinder portion 40 of the controller contacting the tubing.

The open second side wall 18 is then repositioned while journal ends 42 of the controller are inserted into slots 36, 37 on each side wall to form an operative array of the clamp.

The second side wall is snap-locked by pressing the lock plates 20 against the flexible locking caps 52 until the locking caps receive and grip the lock plates to form the closed arrangement of the body.

The lever arm 26 is then actuated by manual rotation until gear teeth 34 which project from the flow controller engage the gear teeth 35 projecting from the second side wall, so that the cylinder portion of the flow controller travels across the bottom wall and squeezes the compressible tubing against the bottom wall, thereby constricting the tubing to a desired flow rate.

The position of the lever arm at the desired flow rate may then be recorded. This record can be done by a simple pencil or marker line on the arcuate bar adjacent the lever arm, such that when the clamp is disassembled and then reinstalled, it can readily be reset to the desired or prescribed flow rate.

While the preferred embodiment of the invention has been disclosed herein, it will be appreciated that modification of this particular embodiment of the invention will be resorted to without departing from the scope of the invention.

What is claimed is:

1. A tubing clamp to control fluid flow through compressible tubing, said clamp having an operative array, an inoperative or molded array, anterior and posterior ends, the tubing clamp comprising:

a body having first and second sidewalls and a bottom wall, said first side wall durably coupled to the bottom wall and the second side wall repositionally coupled to the bottom wall adapting the body to have an open and a closed arrangement, said body in open arrangement adapted for sidewise insertion of tubing therein; and said body in closed arrangement defining a channel open at the top and at both ends;

a hinge for repositionally coupling said second side wall to the bottom wall:

a flow controller having two ends, a cylinder portion having a cylindrical surface at the first end and a lever arm at the second end, said lever arm projecting radially from said cylinder portion to extend outside the channel; said controller removably mounted in the body upon the tubing in the channel to form the operative array of the clamp;

the clamp being constructed of a polymeric material;

wherein the hinge is a living hinge formed of clamp material; and wherein the body and controller are constructed in a one-piece structure to form a molded array for the clamp, wherein said controller is detachably attached to the body by a tear tab formed of clamp material.

2. The tubing clamp of claim 1, wherein journal ends project axially from each side of the cylindrical portion of said flow controller; and, said first and second side walls each have a slot grooved longitudinally therein, the slots disposed to receive said journal ends when the body is in closed arrangement.

3. The tubing clamp described in claim 2, wherein a notch is formed in the sidewall at the posterior ends of each of the slots to facilitate inserting the journal ends into the slots.

4. The tubing clamp described in claim 3, further comprising a row of gear teeth positioned on the circumference of the cylinder portion and projecting axially from the flow controller to engage gear teeth projecting from the second side wall.

5. The tubing clamp defined in claim 4, further comprising an anterior brace projecting from the anterior end of said first side wall, a posterior brace projecting from the posterior end of the first side wall, and an arcuate bar connecting the outer ends of said braces, said arcuate bar coaxial with a transverse line through the center of each of the longitudinal axes of the slots; and, said lever arm adapted for rotation through an arc bounded by said anterior and posterior braces.

6. The tubing clamp described in claim 5, further comprising a lock plate projecting from both the anterior and posterior ends of the second side wall, and a lock arm projecting from the anterior and from the posterior brace near each end of the first side wall, each lock arm having a flexible locking cap at its outer end to receive and grip the lock plates and snap-lock the second side wall essentially parallel to the first side wall and hold the body of said clamp in said closed arrangement.

7. The tubing clamp as defined in claim 6, wherein the lock arms are disposed a sufficient distance from the bottom wall to expedite positioning the tubing over the bottom wall and under each lock arm to guide and hold the compressible tubing in the channel.

8. The tubing clamp of claim 7, wherein the lever projects to the arcuate bar;

a detent projecting from the outer end of the lever arm;

a series of ratchet teeth along the length of the arcuate bar engage the detent to retain the lever arm in place against return rotative movement.

9. The tubing clamp described in claim 8, further comprising means to visually record the position of the lever arm upon the ratchet bar.

10. The tubing clamp described in claim 4, wherein the bottom wall is level from the anterior end to the posterior end of the clamp;

and the longitudinal slots lie in a plane which inclines toward the bottom wall from the posterior end toward the anterior end of the clamp, such that the plane of the slots, if extended, intersects the plane of the bottom wall, if extended.

11. The tubing clamp described in claim 4, wherein the longitudinal slots lie in a plane and the plane of the slots is level from the anterior end to the posterior end of the clamp;

and the bottom wall inclines toward the plane of the slots from the posterior end toward the anterior end of the clamp, such that the plane of the bottom wall, if extended, intersects the plane of the slots, if extended.

12. The tubing clamp of claim 7, wherein said lever arm does not extend to the arcuate bar;

the flow controller retained in a predetermined position against reverse movement by frictional contact of said cylindrical surface of the flow controller with the tubing.

13. A method for controlling flow in a compressible tubing by use of a tubing clamp, said clamp having an operative array, an inoperative or molded array, anterior and posterior ends, the tubing clamp constructed of a polymeric material, with a body having first and second sidewalls and a bottom wall, said first side wall durably coupled to the bottom wall and the second side wall repositionally coupled to the bottom wall adapting the body to have an open and a closed arrangement, said body in open arrangement adapted for sidewise insertion of the tubing therein; and the body in closed arrangement defining a channel open at the top and at both ends;

a living hinge formed of clamp material for repositionally coupling said second side wall to the bottom wall;

a flow controller having two ends, a cylinder portion having a cylindrical surface at the first end and a lever arm at the second end, said lever arm extending radially from said cylinder portion;

said controller adapted to be removably mounted in the body upon the tubing in the channel in the operative array of the clamp;

said body and controller constructed in a one-piece structure to form a molded array/br the clamp, wherein said controller is detachably attached to the body by a tear tab formed of clamp material;

journal ends projecting axially from each side of the cylindrical portion of said flow controller;

said first and second side walls each having a slot grooved longitudinally therein, the slots disposed to receive said journal ends;

a notch formed in the sidewall at the posterior ends of each of the slots to facilitate inserting the journal ends into the slots;

a row of gear teeth positioned on the circumference of the cylindrical portion and projecting axially from the flow controller to engage gear teeth projecting from the second side wall;

said longitudinal slots lying in a plane of the slots, and said plane of the slots being level from the anterior end to the posterior end of the clamp; and the bottom wall inclined toward the plane of the slots from the posterior end toward the anterior end of the clamp, such that the plane of the bottom wall, if extended, intersects the plane of the slots, if extended;

an anterior brace projecting from the anterior end of said first side wall, a posterior brace projecting from the posterior end of the first side wall, and an arcuate bar connecting the outer ends of said braces, said arcuate bar coaxial with a transverse line through the center of each of the longitudinal axes of the slots;

said lever arm adapted for rotation through an arc bounded by said anterior and posterior braces;

a lock plate projecting from both the anterior and posterior ends of the second side wall, and a lock arm projecting from the anterior and the posterior brace adjacent each end of the first side wall, each lock arm having a flexible locking cap at its outer end to receive and grip the lock plates and snap-lock the second side wall essentially parallel to the first side wall and hold the body in the closed arrangement;

said lock arms disposed at a distance from the bottom wall to expedite positioning the tubing over the bottom wall and under each lock arm to guide and hold the compressible tubing in the channel;

said arcuate bar having a series of ratchet teeth along its entire length and a detent which projects from the outer end of the lever arm to engage the ratchet teeth of the arcuate bar and lock the lever arm in place against return rotative movement;

the method comprising the steps of:

breaking the tear tab of the clamp in molded array to separate the flow controller from the body of the clamp;

inserting the tubing sidewise into the body of the clamp while the second sidewall is open and the body is in open arrangement;

positioning the tubing over the bottom wall and under each of the lock arms;

installing the flow controller to overlie the tubing with said cylindrical surface contacting the tubing to form the operative array of the clamp;

repositioning the second side wall with the projecting journal ends of the flow controller in the slots grooved on the side walls;

snap-locking the second side wall to form the closed arrangement of the body with the lock plates under the locking caps of the lock arms.

14. The method for controlling flow of claim 13, further comprising the additional step, after the last step, of:

actuating the lever arm by manual rotation until the gear teeth of the flow controller engage the gear teeth on the second side wall to squeeze the compressible tubing against the bottom wall and constrict the tubing to the desired flow rate.

15. The method for controlling flow of claim 14, further comprising the additional step, after the step of claim 14, of:

recording the flow rate indicator of lever arm position upon the arcuate bar when the desired flow rate is achieved.

* * * * *